(12) United States Patent
Ruyra Baliarda

(10) Patent No.: US 8,992,606 B2
(45) Date of Patent: Mar. 31, 2015

(54) PROSTHETIC DEVICE FOR REPAIRING A MITRAL VALVE

(76) Inventor: Xavier Ruyra Baliarda, Barcelona (ES)

( * ) Notice: Subject to any disclaimer, the term of this patent is extended or adjusted under 35 U.S.C. 154(b) by 0 days.

(21) Appl. No.: 13/635,906

(22) PCT Filed: Mar. 17, 2011

(86) PCT No.: PCT/ES2011/070183
§ 371 (c)(1),
(2), (4) Date: Sep. 18, 2012

(87) PCT Pub. No.: WO2011/113986
PCT Pub. Date: Sep. 22, 2011

(65) Prior Publication Data
US 2013/0053951 A1 Feb. 28, 2013

(30) Foreign Application Priority Data
Mar. 19, 2010 (ES) .................................. 201030407

(51) Int. Cl.
*A61F 2/24* (2006.01)
(52) U.S. Cl.
CPC ....... *A61F 2/2445* (2013.01); *A61F 2220/0025* (2013.01); *A61F 2/2454* (2013.01); *A61F 2/2442* (2013.01); *A61F 2250/0071* (2013.01); *A61F 2230/0071* (2013.01); *A61F 2/2457* (2013.01)
USPC ...................................................... 623/2.36
(58) Field of Classification Search
CPC ............................................ A61F 2250/0071
USPC ............................................... 623/2.36–2.41
See application file for complete search history.

(56) References Cited

U.S. PATENT DOCUMENTS

| | | |
|---|---|---|
| 3,656,185 A | 4/1972 | Carpentier |
| 4,055,861 A | 11/1977 | Carpentier et al. |
| 4,917,698 A | 4/1990 | Carpentier et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,084,151 A | 1/1992 | Vallana et al. |

(Continued)

FOREIGN PATENT DOCUMENTS

| | | |
|---|---|---|
| EP | 0338994 A1 | 10/1989 |
| EP | 1266641 B1 | 10/2004 |

(Continued)

OTHER PUBLICATIONS

Bizzarri, Feederico et al., "Different ways to repair the mitral valve with artificial chordate: a systematic review", Journal of Cardiothoracic Surgery 2010, 5:22, 6 pages.

(Continued)

*Primary Examiner* — Jacqueline Woznicki
(74) *Attorney, Agent, or Firm* — Faegre Baker Daniels LLP

(57) ABSTRACT

Prosthetic band, in particular for repairing a mitral valve, comprising an elongate band made of a flexible material for the fixation of artificial cords, and including a plurality of separable pads that are joined along the trajectory of said elongate band and protrude with respect thereto, said pads being separated from each other and capable of receiving such artificial cords. In this way, the proper length of the artificial cords can be established, and they can be tied without slippage of the knots with the aim of applying them during an operation for the repair of a prolapse of the mitral valve.

10 Claims, 3 Drawing Sheets

(56) References Cited

U.S. PATENT DOCUMENTS

| | | | |
|---|---|---|---|
| 5,104,407 | A | 4/1992 | Lam et al. |
| 5,133,845 | A | 7/1992 | Vallana et al. |
| 5,370,684 | A | 12/1994 | Vallana et al. |
| 5,387,247 | A | 2/1995 | Vallana et al. |
| 5,423,886 | A | 6/1995 | Arru et al. |
| 5,607,471 | A | 3/1997 | Seguin et al. |
| 5,674,279 | A | 10/1997 | Wright et al. |
| 5,716,397 | A | 2/1998 | Myers |
| 5,824,066 | A | 10/1998 | Gross |
| 5,873,812 | A | 2/1999 | Ciana et al. |
| 6,102,945 | A | 8/2000 | Campbell |
| 6,106,550 | A * | 8/2000 | Magovern et al. ........... 623/2.38 |
| 6,143,024 | A | 11/2000 | Campbell et al. |
| 6,217,610 | B1 | 4/2001 | Carpentier et al. |
| 6,250,308 | B1 | 6/2001 | Cox |
| 6,309,414 | B1 | 10/2001 | Rolando et al. |
| 6,406,493 | B1 | 6/2002 | Tu et al. |
| 6,565,603 | B2 | 5/2003 | Cox |
| 6,749,630 | B2 | 6/2004 | McCarthy et al. |
| 6,797,001 | B2 | 9/2004 | Mathis et al. |
| 7,220,227 | B2 | 5/2007 | Sasaki et al. |
| 7,226,477 | B2 | 6/2007 | Cox |
| 8,034,103 | B2 | 10/2011 | Burriesci et al. |
| 8,216,303 | B2 | 7/2012 | Navia |
| 2001/0021874 | A1 | 9/2001 | Carpentier et al. |
| 2001/0039450 | A1 | 11/2001 | Pavcnik et al. |
| 2002/0010504 | A1 | 1/2002 | Alt |
| 2002/0188350 | A1 | 12/2002 | Arru et al. |
| 2003/0083742 | A1 | 5/2003 | Spence et al. |
| 2003/0108264 | A1 | 6/2003 | Nishizawa et al. |
| 2003/0199974 | A1 | 10/2003 | Lee et al. |
| 2003/0208264 | A1 | 11/2003 | McCarthy et al. |
| 2003/0208284 | A1 | 11/2003 | Stewart et al. |
| 2003/0220686 | A1 | 11/2003 | Arru et al. |
| 2004/0039443 | A1 | 2/2004 | Solem et al. |
| 2004/0249453 | A1 | 12/2004 | Cartledge et al. |
| 2005/0004668 | A1 | 1/2005 | Aklog et al. |
| 2006/0129227 | A1 | 6/2006 | Hengelmolen |
| 2006/0149368 | A1* | 7/2006 | Spence ........................ 623/2.37 |
| 2006/0195183 | A1* | 8/2006 | Navia et al. .................. 623/2.18 |
| 2006/0259135 | A1* | 11/2006 | Navia et al. .................. 623/2.11 |
| 2007/0123979 | A1 | 5/2007 | Perier et al. |
| 2007/0162112 | A1 | 7/2007 | Burriesci et al. |
| 2007/0191940 | A1 | 8/2007 | Arru et al. |
| 2009/0088837 | A1 | 4/2009 | Gillinov et al. |
| 2009/0177266 | A1 | 7/2009 | Powell et al. |
| 2010/0042147 | A1 | 2/2010 | Janovsky et al. |
| 2011/0118832 | A1* | 5/2011 | Punjabi ........................ 623/2.36 |

FOREIGN PATENT DOCUMENTS

| | | |
|---|---|---|
| EP | 1348406 B1 | 12/2009 |
| EP | 2198806 A2 | 6/2010 |
| EP | 2548534 A1 | 1/2013 |
| SU | 577022 A1 | 10/1977 |
| WO | 9119465 A2 | 12/1991 |
| WO | WO2005072649 A1 | 8/2005 |
| WO | WO2005082278 A2 | 9/2005 |
| WO | WO2006089236 A1 | 8/2006 |
| WO | WO2006113906 A1 | 10/2006 |
| WO | WO2007072399 A1 | 6/2007 |
| WO | WO2009010619 A2 | 1/2009 |
| WO | WO2009141665 A1 | 11/2009 |
| WO | WO2009133715 A1 | 11/2009 |
| WO | 2011113986 | 9/2011 |

OTHER PUBLICATIONS

Doi, Atsuo et al., "Intracardiac Calipers for Artificial Chordae Replacement in Mitral Valve Repair", The Annals of Thoracic Surgery, 2009, vol. 87, pp. 326-328.

International Search Report and Written Opinion issued in PCT/ES2011/070183, mailed Jul. 29, 2011, 15 pages (with English translations).

Maisano, Francesco et al., "Transapical endovascular implantation of neochordae using a suction and suture device", European Journal of Cardio-thoracic Surgery, No. 36, 2009, pp. 118-123.

Maselli MD, Daniele et al., "A new method for artificial chordate length tuning in mitral valve repair: preliminary experience", The Journal of Thoracic and Cardiovascular Surgery, Aug. 2007, pp. 454-459.

Rankin MD, J. Scott et al., "Adjustable" Artificial Chordal Replacement for Repair of Mitral Valve Prolapse, Ann Thorac Surg 2006, 81, pp. 1526-1528.

Ruyra-Baliarda, Xavier, "Preliminary experience with the no prolapsed system. A new device for ensuring the proper length of artificial chordate in mitral valve repair", Interactive CardioVascular and Thoracic Surgery, No. 10, 2010, pp. 165-167.

International Search Report and Written Opinion issued in PCT/IT2013/000228, mailed May 26, 2014, 12 pages.

Duran, Carlos M. et al., "Techniques for Ensuring the Correct Length of New Mitral Cords", The Journal of Heart Valve Disease, vol. 12, 2013, pp. 156-161.

Supplemental European Search Report issued in EP Application No. 11755736, mailed Jun. 3, 2014, 5 pages.

* cited by examiner

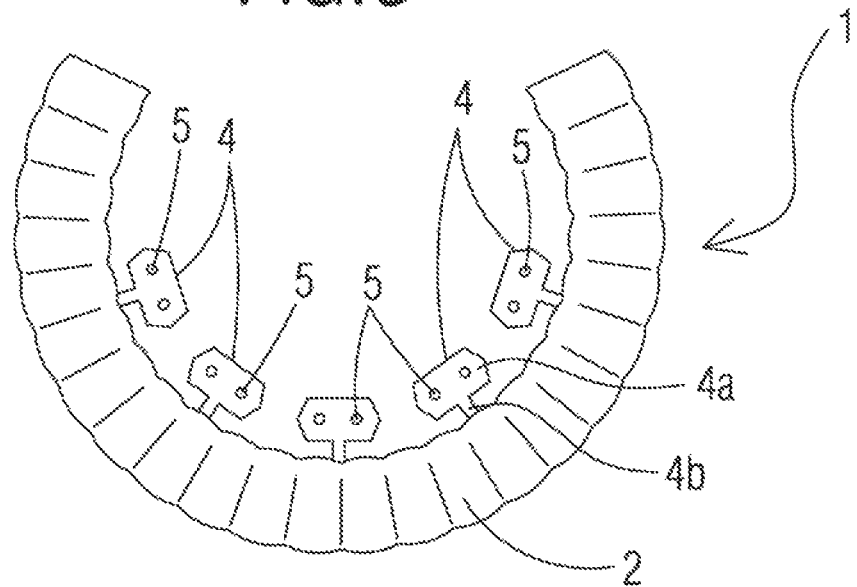
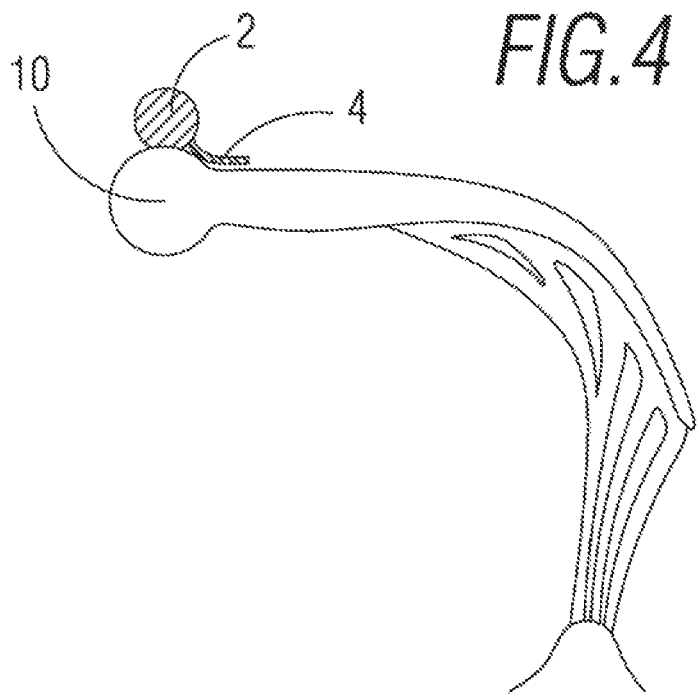

PROSTHETIC DEVICE FOR REPAIRING A MITRAL VALVE

RELATED APPLICATIONS

This application is a U.S. national stage filing under 35 U.S.C. §371 from international patent application number PCT/ES2011/070183, filed on Mar. 17, 2011, which claims priority to Spanish Application No. P201030407, filed Mar. 19, 2010, the contents of which are incorporated herein by reference in their entirety.

BACKGROUND

The present patent application has as its object the provision of a prosthetic band for repairing a mitral valve which incorporates notable innovations and advantages.

More specifically, the invention proposes the development of a prosthetic band designed to facilitate the repair of degenerative mitral insufficiency and having points of reference for the arrangement of artificial cords during the surgical operation.

At present, the main cause of impairment of the mitral valve is degenerative pathology bringing about mitral insufficiency.

The mitral valve is one of the four valves of the heart having a complex structure with various elements which must function in a coordinated manner in order to cause the blood to flow in the correct direction. If the closure of the valve is not adequate, this gives rise to so-called mitral insufficiency.

Basically, the valve consists of two leaflets (anterior and posterior) which are inserted on a ring and anchored to the papillary muscles of the wall of the left ventricle by a large quantity of chordae tendineae (see FIGS. 1 and 2), as can be seen in FIGS. 1 and 2. The normal mitral annulus 10 (see FIG. 4) has a posterior region and an anterior region situated between the two trigones, which are fibrous structures that form part of the base of the heart.

Under normal conditions, during the contraction phase of the heart, those two leaflets come together (coaptation zone) and close the valve, preventing insufficiency from occurring. The closure of the valve is produced practically at the level of the ring and never above it, given that the chordae tendineae do not allow the leaflets to rise above that level.

In mitral insufficiency of a degenerative origin, the closure of the valve is not correct because one of the leaflets, or both of them, move beyond the plane of the ring and penetrate partially into the left atrium, giving rise to what is referred to as prolapse of the leaflets. The primary cause of the prolapse is the elongation or rupturing of one of more of the chordae tendineae.

The most common prolapse is that of the posterior leaflet, but prolapses of the anterior leaflet or of both simultaneously are also common. Relevantly, in mitral insufficiency there always exists a dilatation of the mitral annulus to varying degrees.

When the mitral insufficiency is severe, the patient must undergo surgical intervention. The possibilities are the replacement of the valve with an artificial valve prosthesis, or the repair of the valve itself.

Currently, there is clear evidence that repair is superior to the replacement of the valve in terms of survival, reduction of complications and improvement of the functional status of the patient.

The correct repair of the mitral valve has three objectives:
To restore the mobility of the leaflets without restriction or excess movement;
To create an adequate coaptation surface or closure;
To remodel the shape and size of the dilated mitral annulus.

The repair of the isolated prolapse of the posterior leaflet is simple and reproducible and has traditionally been treated through partial resection of the leaflet. However, when the prolapse is of the anterior leaflet or of both leaflets, the difficulty increases, and many surgeons are unable to repair the valve.

One known and widely used technique consists of the use of artificial cords (hereinafter called "neocords"), usually made of PTFE, which substitute the torn or stretched chordae tendineae. These neocords are stitched to the papillary muscles and extend to the free edge of the leaflets and imitate the function of the natural cords.

The artificial neocords made of PTFE have become the technique of choice for correcting mitral prolapse, and its use has therefore become widespread. Such neocords enable the repair of prolapses of one or both leaflets or of multiple prolapsing segments of the same leaflet, applying as many neocords as necessary.

Nonetheless, the use of these artificial cords is associated with two significant technical problems. One of them consists in the difficulty in measuring the exact shape of the length that the artificial neocords must have, while a second known problem is related to the difficulty in tying the cords over the leaflet while preventing the knots from sliding downward (resulting in the cord being shorter than required and causing overcorrection) due to the slippery nature of the PTFE material.

Various attempts have been made to resolve the aforementioned problems.

SUMMARY

The present invention was developed with the purpose of providing an invention which resolves the abovementioned drawbacks while providing, moreover, other additional advantages which will become evident from the description which follows.

One object of the present invention is therefore to provide a prosthetic band which comprises an elongate band made of a flexible material for the fixation of artificial cords and is characterized in that it includes a plurality of separable pads (preferably made of PFTE) joined along the trajectory of said elongate band which project with respect thereto, which pads are separated from each other and are capable of receiving such artificial cords.

It should be mentioned that these pads act as a point of reference for establishing the correct length of the neocords that are fixed to the elongate band. This is because the distance between the papillary muscles and the mitral annulus remains constant throughout the entire cardiac cycle.

By virtue of these features, the proper length of the neocords can be established, and they can be tied without slippage of the knots with the aim of applying them during an operation for the repair of a prolapse of the mitral valve. Moreover, this is a solution in which no measurement is required either of the size of the ring or band or of the length of the implanted neocords, said prosthetic band being easy to use and handle by the surgeon.

Another advantage of the invention is that, in addition, there is no possibility of slippage of the knots, since tying is performed on the pads, which are fixed to the elongate band and cannot move downward upon being tied.

According to one particularly preferred embodiment of the invention, each of the pads is formed by a substantially laminar main portion and a joining section of lesser thickness that can be fixed to the flexible band, the main portion of the pad also having two through holes through which neocords pass.

Another aspect of the invention which is no less important is that it proves useful for prolapses of a single leaflet (anterior or posterior) or of both leaflets simultaneously and reduces the time required for an operation, thus reducing the risk to the patient.

According to one embodiment of the invention, the pads are joined to the elongate band by an adhesive material.

In one alternative modification of the invention, the pads can be joined to the elongate band by means of stitching.

Other features and advantages of the prosthetic band constituting the object of the present invention will become evident from the non-exclusive description of a preferred embodiment, which is illustrated for the sake of example in a non-limiting manner in the enclosed drawings.

BRIEF DESCRIPTION OF THE DRAWINGS

FIG. 3.—is a plan view of the prosthetic band according to the present invention which adopts a trajectory substantially in the shape of a C;

FIG. 4.—is a schematic elevation in section of the native mitral annulus in which the prosthetic band according to the invention is located.

DETAILED DESCRIPTION

Figure 1:
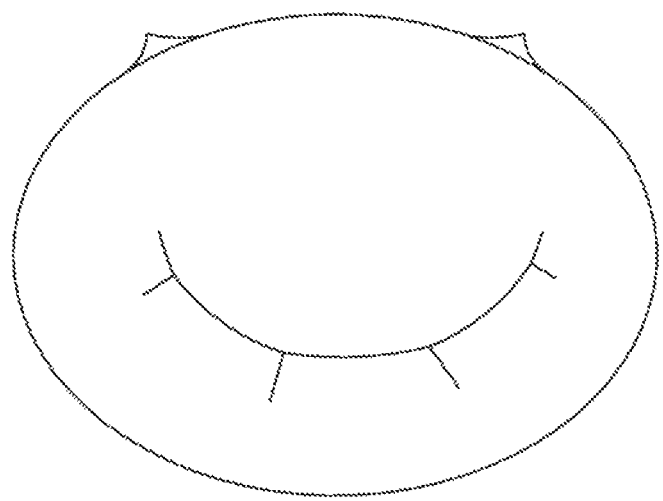
FIG. 1.—is a schematic view of a mitral valve with two leaflets.

As shown in the enclosed figures, a prosthetic band according to the invention is illustrated which is designed for the repair of a mitral valve (represented in FIGS. 1 and 2) using surgical techniques which employ the neocords that were explained above.

Figure 2:
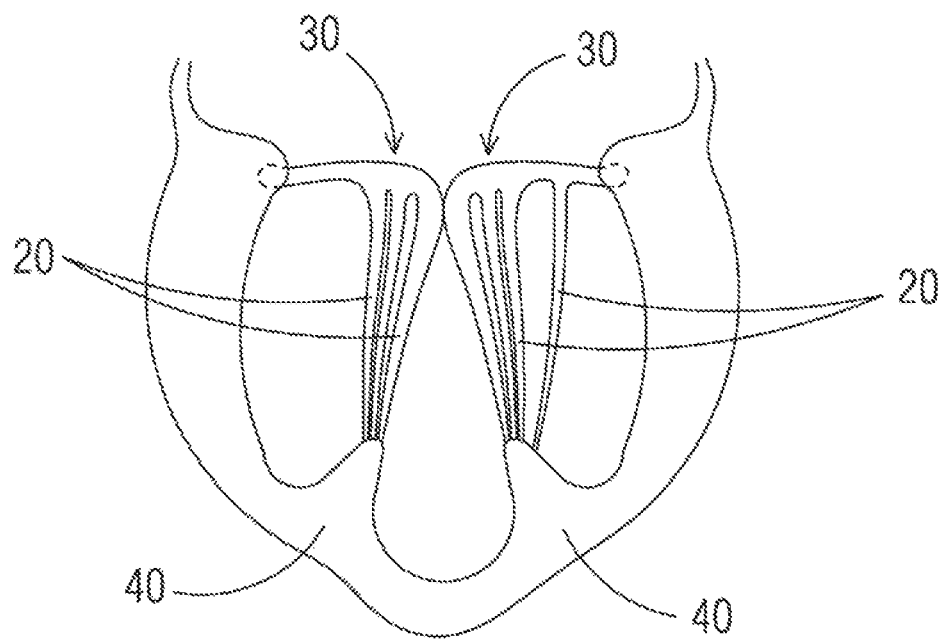
FIG. 2.—is a schematic view of the mitral apparatus showing the left atrial wall, the mitral annulus, two mitral leaflets, multiple chordae tendineae, papillary muscles and the left ventricular wall.

Visible in FIG. 2 are the various parts which make up the mitral apparatus, showing the left atrial wall, the mitral annulus 10, multiple chordae tendineae 20, the mitral leaflets 30 and papillary muscles 40.

More particularly, said prosthetic band 1 comprises an elongate band 2 (having an approximate length of 63 millimeters, which turns out to be ideal for adult patients) made of a flexible material for the fixation of neocords 3 (artificial cords), preferably constituted by a central core of silicone material an exterior covering of polyester material with a circular cross section and an approximate diameter of 3 millimeters. In addition, a plurality of separable pads 4 joined to the band and protruding with respect thereto are provided, said pads 4 being separated from each other and are capable of fixing such neocords 3. All of the pads 4 protrude in the same direction when the elongate band 2 is extended in a straight manner.

As can be seen clearly in FIG. 3, each of the pads 4 is formed by a substantially laminar main portion 4a and a joining section 4b of lesser thickness that can be joined to the flexible band, which facilitates the separation thereof with respect to the main portion 4a, a pair of through holes 5 having been provided in said main portion 4a of the pad 4 through which neocords 3 can pass.

The pads 4 can be joined to the elongate band 2 by an adhesive material, by means of stitching or any other suitable manufacturing means.

The positioning of the prosthetic band with respect to the mitral annulus 10 can be seen in FIG. 4.

The use of the prosthetic band 1 is detailed below with reference to FIGS. 5A-5C, which provide a schematic illustration of the pads 4.

Figure 5A:
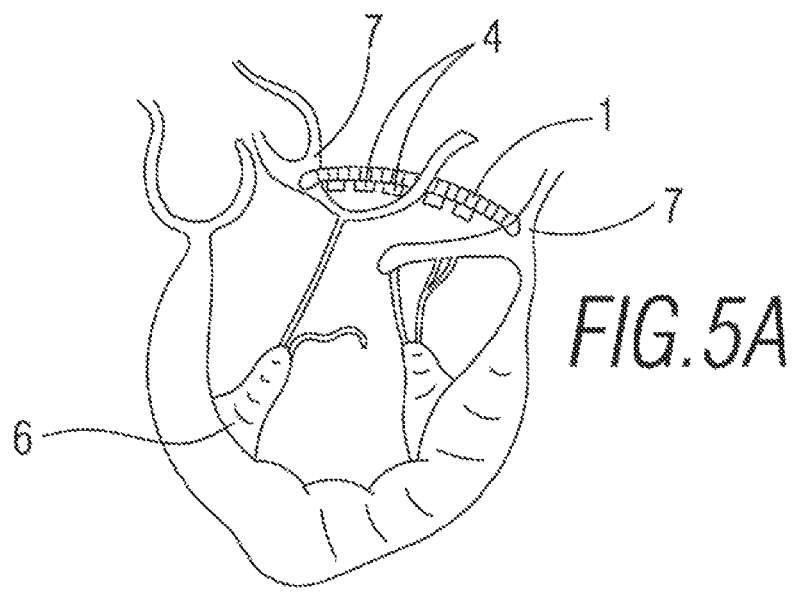
FIG. 5A-5C.—are three schematic views showing the steps in the application of the prosthetic band according to the invention.

In FIG. 5A, the prolapsing segments of both leaflets are identified. One of the ends of the neocord 3 is therefore first stitched to the fibrous head 6 of the papillary muscles 40, leaving the opposite end free. The surgeon then performs an annuloplasty of the posterior ring, with the elongate band 2 of the prosthetic band 1 anchoring its ends in the trigones 7.

Figure 5B:
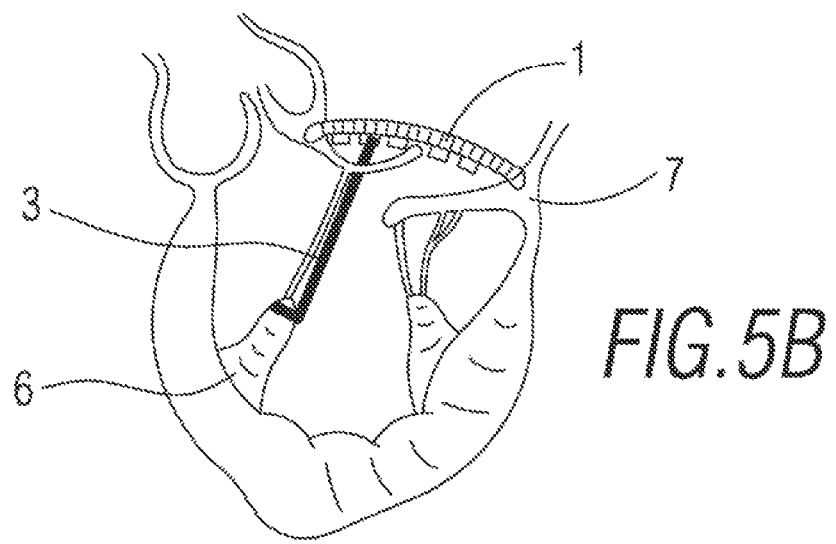
Figure 5C:
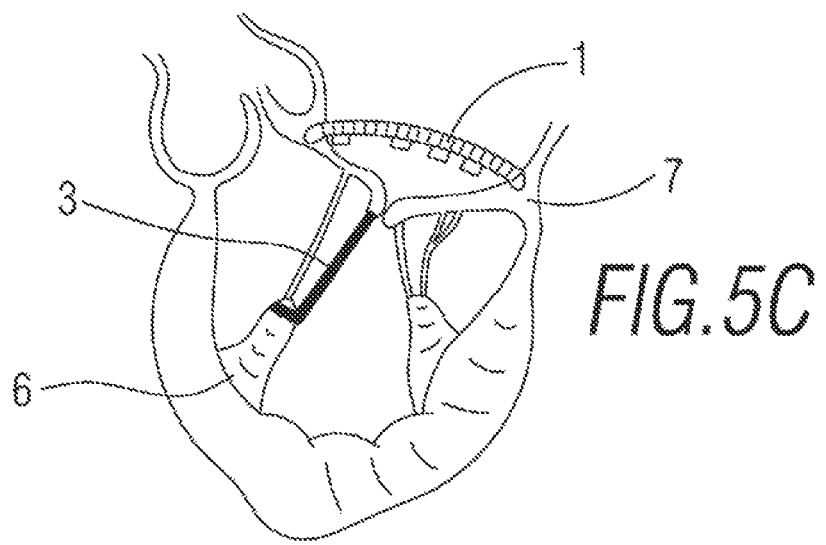

The free end of the neocords is then tied to the pads 4 as can be seen in FIG. 5B.

Finally, the pad is cut, separating it from the elongate band 2, and the pad 4 in question is transferred with its corresponding sutured neocord 3 to the prolapsing segment of the leaflet (see FIG. 5C) and is fixed to same by stitching with a polypropylene suture.

The details, shapes, dimensions and other accessory elements, as well as the materials used in the manufacture of the prosthetic band according to the invention can be substituted as needed with others that are technically equivalent and do not depart from the essence of the invention or the scope defined by the claims, which are included below.

The invention claimed is:

1. An implantable prosthetic device for repairing a mitral valve in a heart, the mitral valve having an annulus, two leaflets, and chordae tendinae, the device comprising:
    an annular body defining a plane and adapted for coupling with the annulus, and:
    one or more pads attached to the annular body and all disposed in the plane defined by the annular body, and extending radially inward from the annular body toward a center of the annulus,
    wherein the pads are adapted to be separated from the annular body after the annular body is implanted within the annulus, and the pads include one or more through holes that are adapted to receive and couple with a portion of one or more artificial cords, such that when the annular body is coupled to the annulus, a first end of the one or more artificial cords is coupled to papillary muscles in the heart and a second end of each artificial cord extends from the papillary muscles to one of the pads and is coupled thereto, such that after the artificial cords are coupled to the pads, the pads are separated from the annular body and are then each coupled to one of the leaflets.

2. The prosthetic device of claim 1 wherein the annular body is an elongate band made of a flexible material.

3. The prosthetic device of claim 1 wherein the pads comprise a substantially planar main portion adapted for contacting one of the leaflets and a joining segment of lesser thickness than the main portion and that is attached to the annular body.

4. The prosthetic device of claim 1 wherein the annular body is arcuate in shape and has two free ends that are separated by an opening.

5. The prosthetic device of claim 4 wherein the pads protrude in the same direction when the annular body is extended in a straight manner.

6. The prosthetic device of claim 1 wherein the annular body is a closed ring.

7. The prosthetic device of claim 1 wherein the one or more through holes comprises two through holes through which the artificial cords pass.

8. The prosthetic device of claim 1 wherein the pads are joined to the annular body by an adhesive material.

9. The prosthetic device of claim 1 wherein the pads are joined to the annular body by sutures.

10. An implantable prosthetic device for repairing a mitral valve in a heart, the mitral valve having an annulus, two leaflets, and chordae tendinae, the device comprising:
   an annular body defining a plane and adapted for coupling with the annulus, and:
   one or more pads attached to the annular body and all disposed in the plane defined by the annular body, and extending radially inward from the annular body toward a center of the annulus, while attached to the annular body, wherein the pads comprise a substantially planar main portion having a first width and a first thickness adapted for contacting one of the leaflets and joining a segment having a second width and a second thickness for attaching the main portion to the annular body,
   wherein one of the second width and the second thickness are less than a corresponding one of the first width and the first thickness, such that the pads are adapted to be separated from the annular body at the joining segment, and the pads include one or more through holes in the main portion that are adapted to receive and couple with a portion of one or more artificial cords, such that when the annular body is coupled to the annulus, the one or more artificial cords are coupled to papillary muscles in the heart and each artificial cord extends from the papillary muscles to one of the pads and is coupled thereto, and configured such that when the artificial cords are coupled to the pads, the pads may be separated from the annular body at the joining segment and then each coupled to one of the leaflets.

* * * * *